(12) United States Patent
Gao et al.

(10) Patent No.: US 8,690,567 B2
(45) Date of Patent: Apr. 8, 2014

(54) ADJUSTABLE ORTHODONTIC BRACKET POSITIONING DEVICE AND METHOD THEREOF

(75) Inventors: Zhuangcun Gao, Qingdao (CN); Xiangyu Gao, Qingdao (CN)

(73) Assignee: Qingdao Shinan Huakang Dental Clinic, Qingdao, Shandong Province (CN)

( * ) Notice: Subject to any disclaimer, the term of this patent is extended or adjusted under 35 U.S.C. 154(b) by 65 days.

(21) Appl. No.: 13/201,463

(22) PCT Filed: Feb. 10, 2010

(86) PCT No.: PCT/CN2010/070593
§ 371 (c)(1), (2), (4) Date: Aug. 15, 2011

(87) PCT Pub. No.: WO2010/102534
PCT Pub. Date: Sep. 16, 2010

(65) Prior Publication Data
US 2011/0300500 A1     Dec. 8, 2011

(30) Foreign Application Priority Data

Mar. 12, 2009   (CN) .......................... 2009 1 0019709

(51) Int. Cl.
*A61C 3/00*   (2006.01)

(52) U.S. Cl.
USPC ............................................................ 433/3

(58) Field of Classification Search
USPC .......... 433/2–4, 153, 155, 157, 159, 162–163
See application file for complete search history.

(56) References Cited

U.S. PATENT DOCUMENTS 4,850,864 A * 7/1989 Diamond ........................ 433/3
6,447,291 B2 * 9/2002 Kim ................................ 433/4

* cited by examiner

*Primary Examiner* — Heidi M Eide (57) ABSTRACT

An adjustable orthodontic bracket-positioning device includes an adjustable bracket-positioning jig, a positioning vernier and a dental crown vernier. First, using the crown vernier to measure the crown height value of patients' tooth, then labeling the measured center height value of clinical dental crown on the positioning vernier, correctly position the adjustable bracket-positioning jig in the groove shaped base of the positioning vernier, and finally use the adjustable bracket-positioning jig to bond MBT bracket.

7 Claims, 5 Drawing Sheets

ADJUSTABLE ORTHODONTIC BRACKET POSITIONING DEVICE AND METHOD THEREOF

BACKGROUND OF THE PRESENT INVENTION

1. Technical Field of the Present Invention

The present invention relates to Orthodontic Treatment, specifically, to an adjustable orthodontic bracket positioning device, method and application.

2. Brief Description of Prior Arts

The incidence ratio of Malocclusion reaches as high as 65% usually and most patients need to accept medical intervention or orthodontic treatment. Straight wire appliance is the advanced development of the edgewise appliance, which retains the characteristics of the edgewise appliance not only, but also has the strong points of the begg line appliance, which is thin line, slight force and, and therefore become a widely used orthodontics. In the US, more than 80% orthodontists adopt this technique, especially MBT straight wire appliance (the third generation straight wire appliance), which is the newest and most advanced diorthosis.

The key point of operating the MBT straight wire appliance is to bond the bracket onto the center of the clinical crown, so that this can help orthodontists achieve a consistent, anticipated and best medical effect. Orthodontists opine that the best treatment effect in upcoming future will be attributable to those who are proficient in bonding the bracket in place, rather than to those who bended the wire the best in the past.

The existing positioning have the following two methods: one is using eye measurement to position the center of clinical crown and to bond the bracket; the other one is determining the bracket position according to the height of the clinical crown, and then using light cure adhesive to position and bond the bracket by means of a positioning gauge. The eye measurement, however, causes more errors and might increases the possibility of re-bonding the bracket by 50%-60%, even if easy to do. The second method is more precise than the first one, but time consuming, effort consuming and still not that precise sometimes. Therefore, looking for a better bracket-positioning method is desirable.

SUMMARY OF THE PRESENT INVENTION

The objective of the present invention is to furnish an adjustable orthodontic bracket positioning device, a method and application thereof, which can overcome the shortcomings of the existing techniques and position a MBT bracket more conveniently, fast and precisely.

The positioning device of the present invention comprises an adjustable bracket positioning jig, a positioning vernier and a dental crown vernier, wherein the adjustable bracket positioning jig comprises a sliding base with a slideway, a height adjustment device comprised of a slide block slidingly fixed on the sliding base, and an angle adjustment device, which employs a bracket fixed on the sliding base. The sliding base and the slide block are connected via the internal screw threads in a threaded rod and the sliding base, so that a position relation between the two can be adjusted. There is a driving wheel in a driving wheel groove near the height adjustment button at one end of the threaded rod, the driving wheel pushing the slide block to move back and forth along the sliding base. The angle adjustment device comprises a shaft going through the shaft sleeve, with a positioning needle knife at one end. A stop sheet is fixed at the stop pin against the shaft sleeve. A dial is fixed at the other end plane of the shaft sleeve. An angle needle is fixed at the shaft at an area against the dial. An angle adjustment button is fixed at the other end of the shaft. An upper of the shaft sleeve is fixed in a middle of the horizontal part of a stand. Ends of two arms of a V-shaped reference line stand are respectively fixed on the stand. A reference line goes through the reference line hole at the positioning needle knife and the reference line aperture track on the slide block. One end of the reference line is fixed on a top of the V-shaped reference line stand, and the other end is fixed on a middle part of a front end surface of the sliding base, as the reference line of positioning the angle of MBT bracket.

The dental crown vernier, as the initial reference of measuring the height of a clinical dental crown, comprises a main ruler with a rectangular cross-section, which goes through a secondary ruler with a groove structure and slide up and down relatively therein. The main ruler is provided with a reference stand even with the zero graduation line of the secondary ruler; the secondary ruler is provided with a blot for positioning the main ruler.

The basic structure of the vernier part of the positioning vernier and the dental crown vernier is the same, including a main ruler and a secondary ruler, both with graduations and sliding up and down in relation with each other, but the zero graduation line of only the main ruler having a short and suitable distance from the reference surface. The verniers, specifically, the lower part of the secondary ruler of the positioning vernier is fixed on the base stand of the groove shaped base, the groove shaped base being provided with a stop block inside for determining the right position of the adjustable bracket positioning jig.

In consideration of the similar structure of the positioning vernier and the dental crown vernier, and of simplifying the present invention, it is not difficult to combine the two verniers into one. The most direct way is to replace the vernier part of the positioning vernier with the dental crown vernier and connected to the base stand, so that it is to install and detach. Therefore, the present invention will comprise two main parts: one is the adjustable bracket positioning jig and the other is a detachable positioning vernier.

The above-mentioned two alternatives of the orthodontic bracket positioning device can be applied well in the straight wire appliance and the edgewise appliance.

Apparently, the present invention can decrease 50%-60% of possibility of re-bonding the bracket, compared with the eye measurement method. Compared with the second bracket positioning method mentioned above, the present invention improves greatly in terms of time saving, effort saving and positioning precision. The present invention can measure precisely the height of the center clinical dental crown for any one teeth, and then position the bracket based on the measurement value. Therefore, it has solved the key problem of precisely positioning MBT bracket in orthodontic treatment, which can reach a high-quality treatment effect, as well as the bottle-neck problem of limiting the wide application of MBT straight wire appliance. The present invention has the following 4 characteristics:

1. two-way adjustable positioning makes the bracket positioned more precisely;
2. can be used in any race or any individual and therefore treat individually;
3. shorten the operation time of bonding the bracket, which lessens the labor intensity, and then cost down greatly;
4. not only fit for straight wire appliance (including Andrews, Roth, MBT, Tip-Edge and etc.), but also for edgewise appliance; therefore, it can be widely used.

The present invention can reduce or avoid greatly repetitive dental treatment resulting from incorrect bonding brackets, and further reduce the risk of absorption of root of tooth. Thus, it can make a high-quality treatment effect, shorten treatment period, give patients more comfort, and likely become an indispensable tool for dentists using MBT appliance.

1—sliding base; 2—threaded rod; 3—reference line aperture track; 4—positioning needle knife; 5—needle at groove center; 6—reference line hole; 7—reference line stand; 8—shaft; 9—stop pin; 10—stop sheet; 11—angle needle; 12—dial; 13—angle adjustment button; 14—slike block; 15—height adjustment button; 16—shaft sleeve; 17—stand; 18—reference line; 19—reference stand; 20—sliding track; 21—driving wheel; 22—driving wheel groove; 23—threade rod groove; 24—slideway; 25—inner screw thread; 26—secondary ruler; 27—main ruler; 28—stop block; 29—groove-shaped base; 30—reference surface; 31—base stand; 32—bolt; 33—ruler; 34—reference stand; 35—zero baseline; 36—bolt; 37—secondary ruler; 38—adjustable bracket-positioning bracket; 39—angle adjustment device; 40—height adjustment device; 41: positioning vernier; 42—dental crown vernier.

DETAILED DESCRIPTION OF PREFERRED EMBODIMENTS

Figure 1:
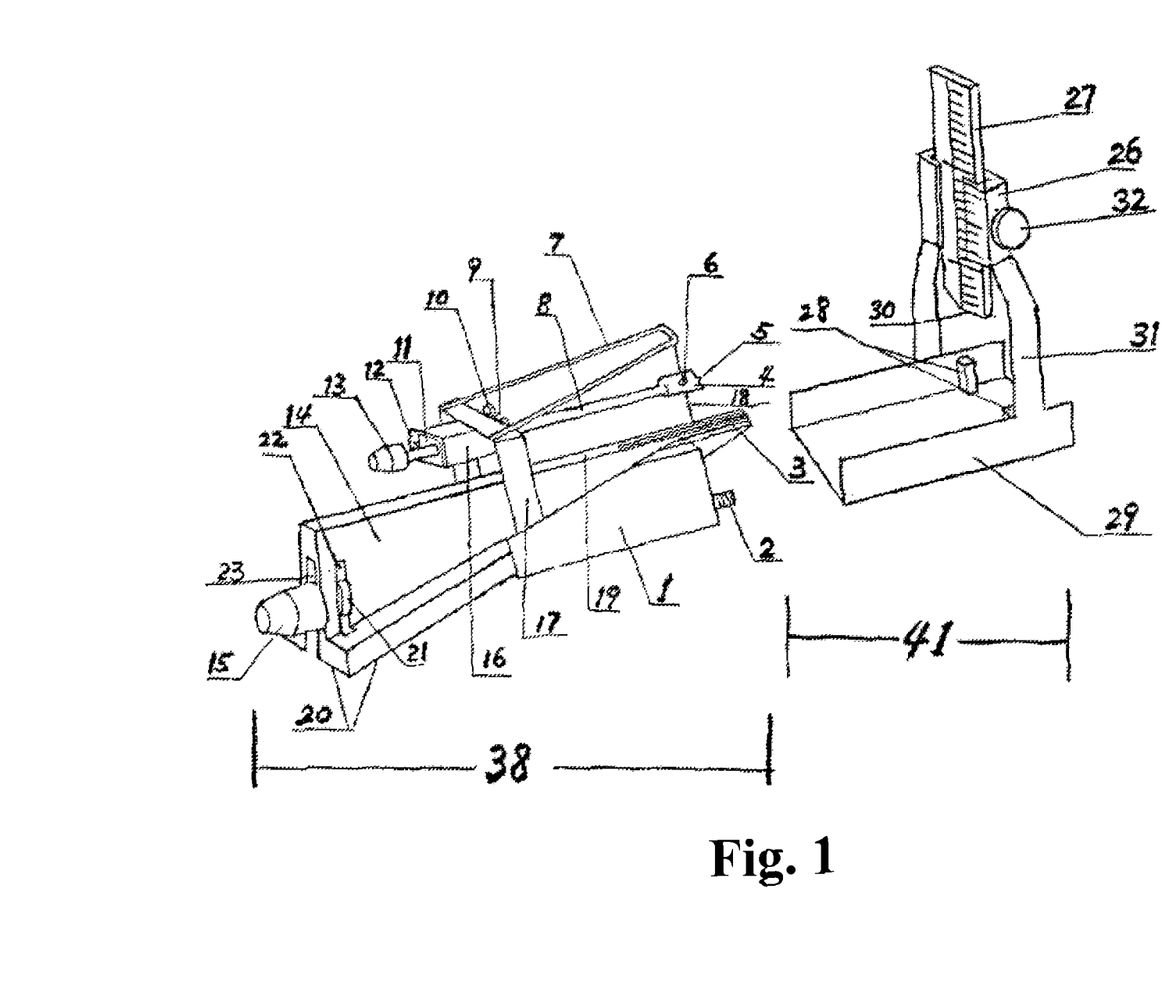
FIG. 1 shows a schematic explosive diagram of an adjustable bracket positioning jig and a positioning vernier.
Figure 5:
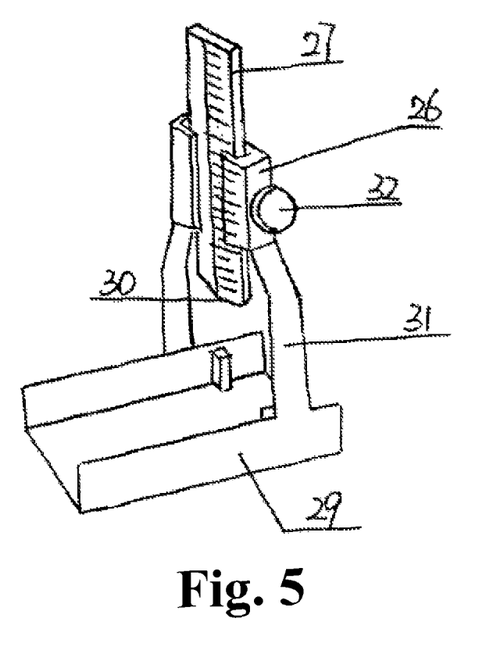
FIG. 5 shows a schematic diagram of the positioning vernier.
Figure 6:
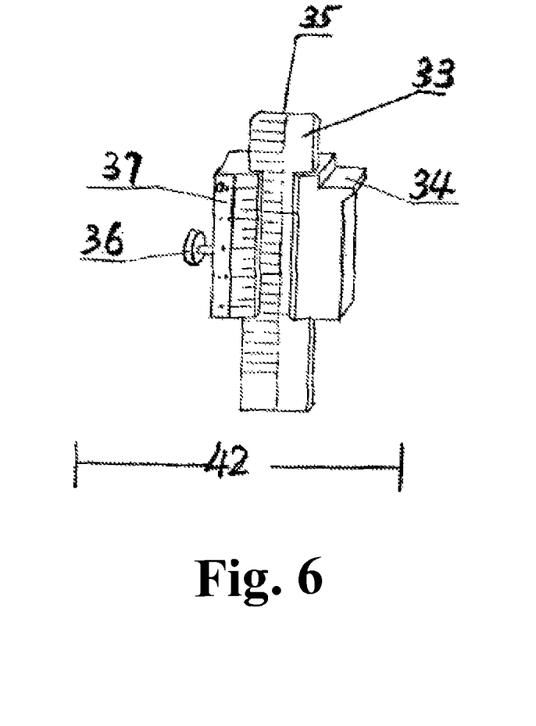
FIG. 6 shows a schematic diagram of a dental crown vernier.

As FIG. 1, FIG. 5 and FIG. 6 show, the present invention comprises an adjustable bracket positioning jig 38, a positioning vernier 41 and a dental crown vernier 42.

As FIG. 1 shows, the adjustable bracket positioning jig 38, as the main part of the present invention, comprises a sliding base 1 with a slideway 24, a height adjustment device 40 comprised of a slide block 14 slidingly fixed on the sliding base 1, and an angle adjustment device 39, which employs a stand 17 fixed on the sliding base 1.

Figure 4:
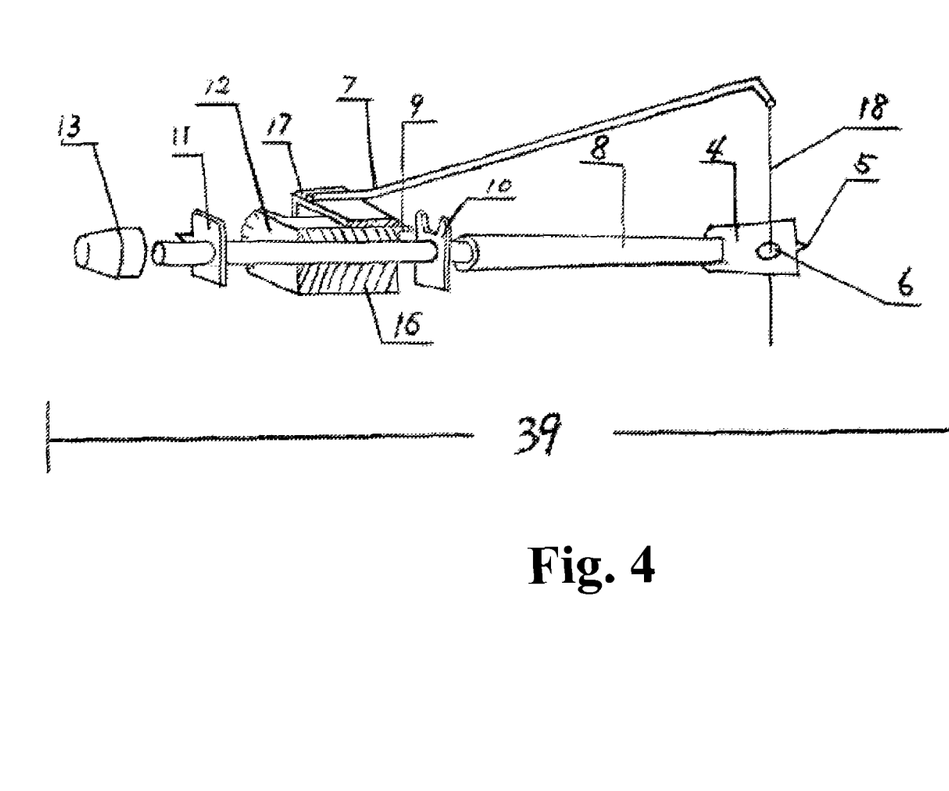
FIG. 4 shows a schematic diagram of an angle adjustment device.

The sliding base 1 and a slide block 14 are connected via the internal screw threads 25 in a threaded rod 2 and the sliding base 1, so that a position relation between the two can be adjusted. A driving wheel 21 is set in a driving wheel groove 22 near the height adjustment button 15 at one end of the threaded rod 2, the driving wheel 21 pushing the slide block 14 to move back and forth along the sliding base 1. As FIG. 4 shows, an angle adjustment device 39 comprises a shaft 8 going through a shaft sleeve 16, with a positioning needle knife 4 at one end. A stop sheet 10 is fixed at a stop pin 9 abutting against the shaft sleeve 16, the stop sheet 10 and the stop pin cooperating together to limit the spinning of the shaft when overspeeding. A dial 12 is fixed at the other end plane of the shaft sleeve 16. An angle needle 11 is fixed on the shaft 8 at an area against the dial 12. An angle adjustment button 13 is fixed at the other end of the shaft 8. The upper of the shaft sleeve 16 is fixed in a middle of the horizontal part of the stand 17. Ends of two arms of a V-shaped reference line stand 7 are respectively fixed on the stand 17. A reference line 18 goes through the reference line hole 6 on the positioning needle knife 7 and the reference line aperture track 3 on the slide block 14. One end of the reference line 18 is fixed on a top of the V-shaped reference line stand 7, and the other end is fixed on a middle part of the front end surface of the sliding base 1 in order to replace the virtual long axis, as the reference line of positioning the angle of MBT bracket.

As FIG. 6 shows, a dental crown vernier 42, as the initial reference of measuring the height of a clinical dental crown, comprises a main ruler 33 with a rectangular cross-section, which goes through a secondary ruler 37 with a groove structure. It means that the main ruler 33 and the secondary ruler 37, both with graduations, slide up and down in relation to each other. The main ruler 33 is provided with a reference stand 34 at the place even with the zero graduation line of the secondary ruler 37. The secondary ruler 37 is provided with a bolt 36 for positioning the main ruler 33.

As FIG. 5 and FIG. 6 show, the basic structure of the vernier part of the positioning vernier 41 and the dental crown vernier 42 is the same, which includes a main ruler 27 and a secondary ruler 26, both with graduations and sliding up and down in relation with each other. A lower part of the secondary ruler 26 is fixed on the base stand 31 of a groove shaped base 29, and the groove shaped base is provided with a stop block 28 inside for determining the right position of the adjustable bracket positioning jig 38.

The above-described sideway 24 and sliding track 20 can be designed as the structure of combination of dovetail groove and dove tenon. The positioning needle knife 4 can be a magnetic substance made of permanent magnetic material, which matches the bracket made of magnetic materials. In other words, when the above-mentioned positioning needle knife 4 is made of magnetic materials, which is a magnetic substance, the corresponding bracket should be selected from magnetic stainless steel materials that can be magnetized by the positioning needle knife, so that the bracket can be precisely magnetized from outside of mouth onto the positioning needle 4, and then be operated more conveniently in the mouth.

As another embodiment, the adjustable orthodontic bracket positioning device of the present invention are comprised of two main part: the adjustable bracket positioning jig 38 and the positioning vernier 41.

The positioning method of the present invention is also called MBT bracket positioning method.

First, use the dental crown vernier to measure the height of a clinical dental crown, make the reference stand of the vernier and the inciso ridge or buccal dental cusp of the measured dental crown in contact with each other, and then make the zero baseline of the dental crown vernier just in contact with the intersection of the dental cervix and the crown axis. The measured value is the height of clinical dental crown, wherein the ½ is the center height of clinical crown.

The next, label a measured center height value of clinical crown on the positioning vernier, then correctly position the adjustable bracket positioning jig in the groove shaped base of the positioning vernier. Twist the height adjustment button in order to make a reference stand of the adjustable bracket positioning jig raised to be in contact with a reference surface of the positioning vernier. At this time, the distance of the needle at a center of the groove and the reference stand is equivalent to the measured center height value of clinical crown, and the labeled center height value of clinical dental crown on the positioning vernier is shifted to the adjustable bracket positioning jig.

Finally, use the adjustable bracket positioning jig to bond the MBT bracket. The specific steps are as follows. First, place approximately a bracket covered with adhesive to the center of the dental crown, slightly away from the inciso ridge or the buccal dental cusp; insert the positioning needle knife inside the groove of the bracket and aim the needle of the groove center at the center of the bracket; meanwhile, make the reference stand and the inciso ridge or buccal dental cusp in close contact; then align the reference line with the dental crown axis. At this time, the needle of the groove center, the center of the bracket and the center of clinical dental crown are in the same height; moreover, the center of the bracket and the center of clinical dental crown are coincided. Then, twist the angle adjustment button in order to make the vertical axis of the bracket and the reference line coincided. At this moment, the MBT bracket has been precisely placed at the center of clinical dental crown.

Take the right maxillary central incisor as an example. During using, make the reference stand 34 of the crown vernier and the inciso ridge of the dental crown in contact. Make the zero baseline 35 just in contact with the intersection of the dental cervix and the crown axis. The measured value 8.64 mm is the height of clinical dental crown, wherein the ½, namely 4.32 mm, is the center height of clinical crown.

Take the right maxillary second premolar as an example. During using, make the reference stand 34 of the crown vernier 42 and the buccal dental cusp of the measured dental crown in contact. Make the zero baseline 35 just in contact with the intersection of the dental cervix and the crown axis. The measured value 6.32 mm is the height of clinical dental crown value, wherein the ½, namely 3.16 mm, is the center height value of clinical crown.

Label the measured center height value 4.32 mm (3.16 mm) of clinical crown on the positioning vernier 41. Place the adjustable bracket positioning jig 38 precisely on the groove shaped base 29 of the positioning vernier 41. Twist the height adjustment button 15 to make the reference stand 19 raised till in contact with the reference surface 30 of the positioning vernier 41. At this time, the labeled center height of clinical crown on the positioning vernier 41 can be shifted to the adjustable bracket positioning jig 38.

As FIG. 1 shows, when using the adjustable bracket positioning jig 38 to bond MBT bracket, place approximately a bracket covered with adhesive to the center of the dental crown first, slightly away from the inciso ridge or the buccal dental cusp. Then, insert the positioning needle knife 4 inside the groove of the bracket and aim the needle 5 of the groove center at the center of the bracket. Meanwhile, make the reference stand 19 and the inciso ridge or buccal dental cusp in close contact; then align the reference line 18 with the dental crown axis. At this time, the needle 5 of the groove center, the center of the bracket and the center of clinical dental crown are in the same height; moreover, the center of the bracket and the center of clinical dental crown are coincided. Further, twist the angle adjustment button 13 in order to make the vertical axis of the bracket and the reference line 18 coincided. At this moment, the MBT bracket has been precisely placed at the center of clinical dental crown. If using chemical curing adhesive, don't take away the adjustable bracket positioning jig before the adhesive cures. If using light cure adhesive, it should be noticed to carefully withdraw from the adjustable bracket positioning jig and keep the bracket in the correct place, and then proceed with light cure.

Figure 2A:
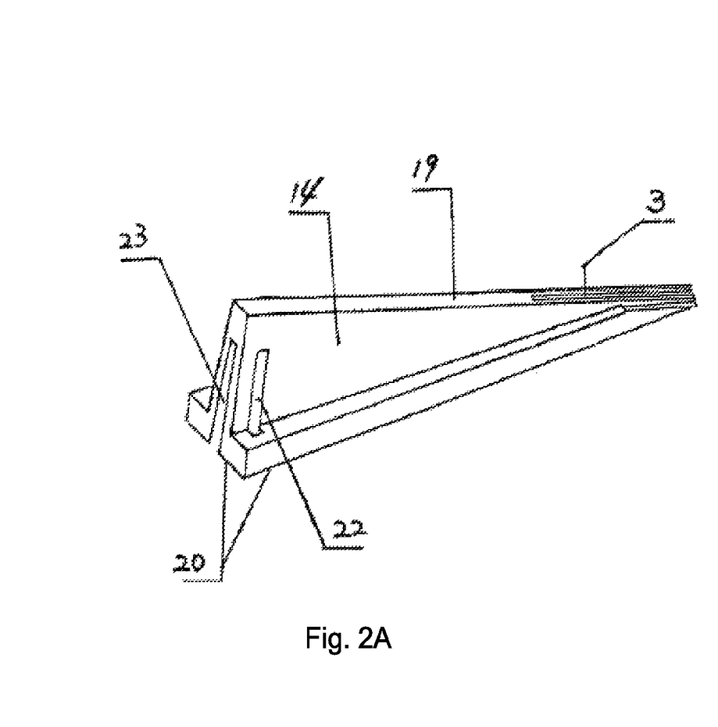
FIG. 2A shows a first part of the adjustable bracket positioning jig.
Figure 2B:
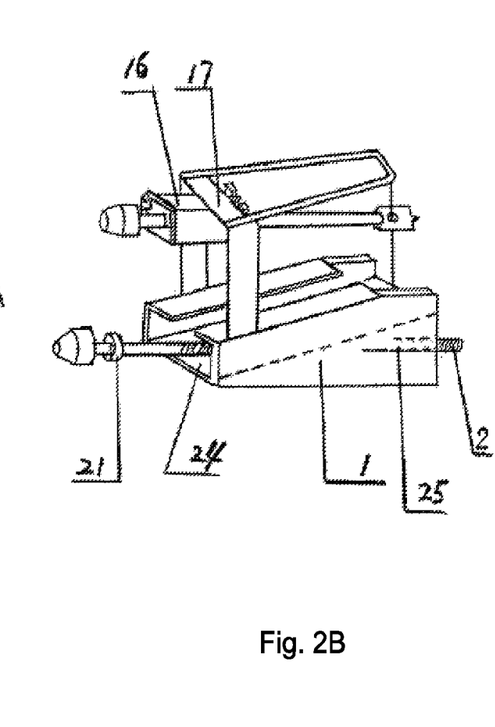
FIG. 2B shows a second part of the adjustable bracket positioning jig.
Figure 3:
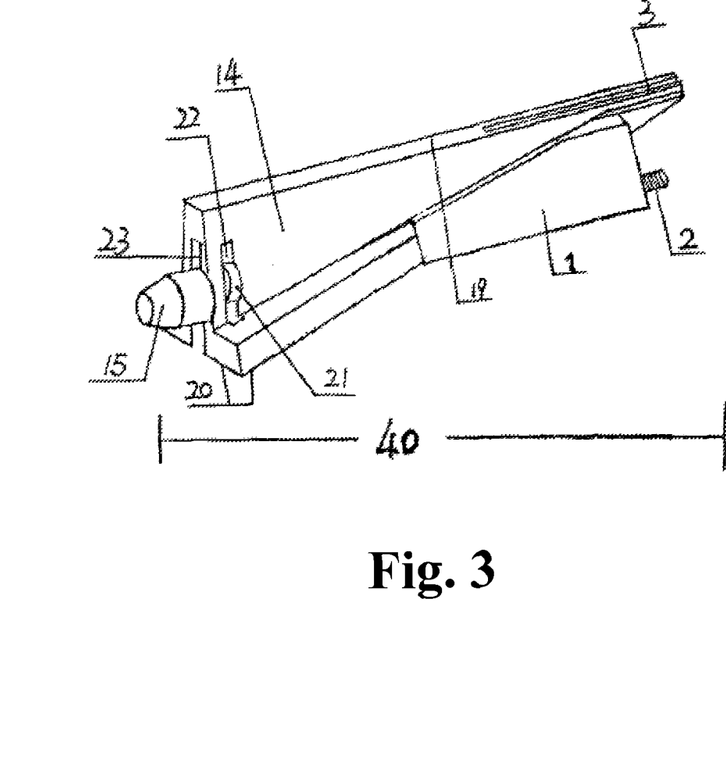
FIG. 3 shows a schematic diagram of a height adjustment device.

As FIG. 2 shows, the adjustable bracket positioning jig can be changed in any height and any angle within a predetermined range. The reference line 18 of the angle adjustment device 39 is an important reference. By using the reference line 18 to replace the virtual long axis and as the reference of positioning the angle of the MBT bracket, clinical operation become more visual and bracket positioning become more precise.

As FIG. 5, FIG. 6 show, the basic structure of the positioning vernier 41 and the dental crown vernier 42 is the same in the vernier part. The structure and principle are the similar with a vernier caliper, with the difference of the main ruler 27 (33) of the former two verniers being slidable and secondary ruler 26 (37) being fixed, while the vernier caliper being the opposite, its main ruler being fixed and the secondary ruler being slidable.

The adjustable bracket positioning jig, the positioning vernier and the dental crown vernier of the present invention can be applied in practice with the following technical precision requirement.

The slideway 24 and sliding track 20 are precise sliding fit. The shaft 8 and shaft sleeve 16 of the angle adjustment device 39 are precise running fit. The positioning vernier 41 and the main ruler 27 (33) and secondary ruler 26 (37) are precise sliding fit.

The adjustable bracket positioning jig 38 can be changed in the range of 2.0 mm-6.5 mm to obtain a required bracket height. With the clinical crown center as the center of a circle (namely the center of the bracket), the MBT bracket can be revolved at will within the range of 25 degree of the left and right side of the long axis of the dental crown, and then positioned precisely.

The measurement range of the positioning vernier is 0~10 mm, and the precision is 0.08 mm. The measurement range of the dental crown vernier is 0 mm~20 mm and the precision is 0.08 mm. The present vernier can be direct used for measurement in mouth, or indirectly in a dental stone model. The dental crown vernier 42 and the positioning vernier 41 can adopt the precision around 0.1 mm.

The reference line 18 uses stainless steel with a 0.08~0.20 mm diameter. The width of the reference line aperture track is around 0.5 mm. The width and thickness of the stainless steel positioning needle knife 4 should fit the groove of the bracket. The working end of the positioning needle knife takes on a knife-edge. The needle 5 of the groove center shows a needle shape and protrudes 0.5 mm outward.

Apparently, the above-mentioned two embodiments of the adjustable orthodontic bracket positioning device can be widely applied in bracket positioning and likely become the right-hand tool for those dentists who operate MBT straight wire appliance.

What is claimed is:

1. An adjustable orthodontic bracket-positioning device, comprising an adjustable bracket-positioning jig (38);
    a positioning vernier (41); and
    a dental crown vernier (42),
    wherein the adjustable bracket-positioning jig (38) comprises
    a sliding base (1) with a slideway (24);
    a height adjustment device (40) comprised of a slide block (14) fixed on the sliding base (1), and
    an angle adjustment device (39) fixed to the sliding base through a bracket;
    the sliding base (1) and the slide block (14) are connected through internal screw threads (25) in a threaded rod (2)

and the sliding base (1), so that a position relation between the sliding base and slide block is capable of being adjusted;

a driving wheel (21) in a driving wheel groove (22) near a height adjustment button (15) at one end of the threaded rod (2), the driving wheel is capable of pushing the slide block to move back and forth along the sliding base;

the angle adjustment device (39) comprises a shaft (8) going through a shaft sleeve (16), with a positioning needle knife (4) at one end of the shaft;

a stop sheet (10) fixed on a stop pin against one end of the shaft sleeve (16);

a dial (12) fixed at the other end of the shaft sleeve (16);

an angle needle (11) fixed at the shaft (8) at an area against the dial (12);

an angle adjustment button (13) fixed at the other end of the shaft (8);

an upper surface of the shaft sleeve (16) is fixed horizontally in a middle part of a stand (17);

a V-shaped reference line stand (7) comprising two arms, wherein ends of the two arms are respectively fixed on the stand (17);

a reference line (18) extending through a reference line hole (6) at the positioning needle knife (4) and a reference line aperture track (3) on the slide block (14);

wherein one end of the reference line (18) is fixed on a top of the V-shaped reference line stand (7), and the other end of the reference line is fixed on a middle part of a front end surface of the sliding base (1) wherein the reference line is used as a reference line for positioning a MBT bracket;

the dental crown vernier (42), for measuring a height of a clinical dental crown, comprises a main ruler (33) with a rectangular cross-section, extending through a secondary ruler (37) with a groove structure;

the main ruler is provided with a reference stand (34) even with a zero graduation line of the secondary ruler (37);

the secondary ruler (37) is provided with a bolt (36) for positioning the main ruler (33);

the positioning vernier (41) comprises a main ruler (27) and a secondary ruler (26), both the main ruler and the secondary ruler comprise graduations and are capable of sliding up and down in relation with each other;

a lower part of the secondary ruler (26) of the positioning vernier (41) is fixed on a base stand (31) of a groove shaped base (29), and a stop block is set in the groove shaped base.

2. The adjustable orthodontic bracket-positioning device set forth in claim 1, wherein the positioning needle knife (4) comprises a magnetic substance made of permanent magnetic material.

3. The adjustable orthodontic bracket-positioning device set forth in claim 1, wherein the slideway (24) comprises a dovetail groove and a sliding track (20) of the slide block (14) comprises a dove tenon capable of being received in the dovetail groove.

4. A method of using then adjustable orthodontic bracket-positioning device set forth in claim 1, comprising:
using the dental crown vernier (42) to measure a center height value of a clinical dental crown;
labeling the center height value of clinical dental crown on the positioning vernier (41);
positioning the adjustable bracket-positioning jig in the groove shaped base (29) of the positioning vernier (41);
twisting the height adjustment button (15) making a reference stand (19) of the adjustable bracket-positioning jig (38) rise to contact a reference surface (30) of the positioning vernier (41); when the reference stand is in contact with the reference surface of the positioning vernier, the distance of the needle (5) and the reference stand (19) is equivalent to the measured center height value of the clinical dental crown, and the labeled center height value of clinical dental crown on the positioning vernier is shifted to the adjustable bracket-positioning jig; and
using the adjustable bracket-positioning jig to bond the MBT bracket to the clinical dental crown.

5. An adjustable orthodontic bracket-positioning device, comprising an adjustable bracket-positioning jig (38); and
a positioning vernier (41),
wherein the adjustable bracket-positioning jig (38) comprises
a sliding base (1) with a slideway (24);
a height adjustment device (40) comprised of a slide block (14) fixed on the sliding base (1), and
an angle adjustment device (39) fixed to the sliding base through a stand;
the sliding base (1) and the slide block (14) are connected through internal screw threads (25) in a threaded rod (2) and the sliding base (1), so that a position relation between the sliding base and slide block is capable of being adjusted;
a driving wheel (21) in a driving wheel groove (22) near a height adjustment button (15) at one end of the threaded rod (2), the driving wheel is capable of pushing the slide block to move back and forth along the sliding base;
the angle adjustment device (39) comprises a shaft (8) going through a shaft sleeve (16), with a positioning needle knife (4) at one end of the shaft;
a stop sheet (10) fixed on a stop pin against one end of the shaft sleeve (16);
a dial (12) fixed at the other end of the shaft sleeve (16);
an angle needle (11) fixed at the shaft (8) at an area against the dial (12);
an angle adjustment button (13) fixed at the other end of the shaft (8);
an upper surface of the shaft sleeve (16) is fixed horizontally in a middle part of a stand (17);
a V-shaped reference line stand (7) comprising two arms, wherein ends of the two arms are respectively fixed on the stand (17);
a reference line (18) extending through a reference line hole (6) at the positioning needle knife (4) and a reference line aperture track (3) on the slide block (14);
wherein one end of the reference line (18) is fixed on a top of the V-shaped reference line stand (7), and the other end of the reference line is fixed on a middle part of the front end surface of the sliding base (1) in order to replace a virtual long axis, wherein the reference line is used as a reference line for positioning a MBT bracket;
the positioning vernier (41) comprises a dental crown vernier (42), a groove shaped base (29) and a base stand (31);
the vernier part comprises a main ruler (33) and a secondary ruler (37), both of the main ruler and the secondary ruler comprise graduations and are capable of sliding up and down in relation with each other;
a lower part of the secondary ruler (37) is fixed on a base stand (31) comprising a groove shaped base (29), and a stop block being set in the groove shaped base.

6. The adjustable orthodontic bracket-positioning device set forth in claim 5, wherein the positioning needle knife (4) comprises a magnetic substance made of permanent magnetic material.

7. The adjustable orthodontic bracket-positioning device set forth in claim 5, wherein the slideway (24) comprises a dovetail groove and a sliding track (20) of the slide block (14) comprises a dove tenon capable of being received in the dovetail groove.

* * * * *